US00PP17623P2

(12) United States Plant Patent
Bergman

(10) Patent No.: US PP17,623 P2
(45) Date of Patent: Apr. 17, 2007

(54) ***HIBISCUS* PLANT NAMED 'YOHIB 2362'**

(50) Latin Name: *Hibiscus rosa-sinensis*
Varietal Denomination: YOHIB 2362

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 50 days.

(21) Appl. No.: 11/177,972

(22) Filed: Jul. 8, 2005

(51) Int. Cl.
*A01H 5/00* (2006.01)

(52) U.S. Cl. ..... Plt./257
(58) Field of Classification Search ..... Plt./257
See application file for complete search history.

(56) References Cited

PUBLICATIONS

UPOV–ROM GTITM, Plant Variety Database, 2006/01, GTI Jouve Retrieval Software, Citation for *Hibiscus* 'Yohib 2362' one page.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct *Hibiscus* plant named 'YOHIB 2362', characterized by its compact, upright, outwardly spreading, uniform, dense and symmetrical plant habit that is appropriate for container production; glossy dark green-colored leaves; uniform and freely flowering habit; large bright yellow-colored flowers with dark red-colored centers; good resistance to flower bud abscission during shipping; and tolerance to pathogens common to *Hibiscus* grown under Florida production conditions.

1 Drawing Sheet

Botanical designation: *Hibiscus rosa-sinensis.*
Cultivar denomination: 'YOHIB 2362'.

CROSS-REFERENCE TO RELATED APPLICATIONS

The present application is co-pending with the following related applications: *Hibiscus* Plant Named 'Montego Wind' (U.S. Plant patent application Ser. No. 11/178,026); Wendy R. Bergman, Applicant.

BACKGROUND OF THE INVENTION

The present invention relates to a new and distinct cultivar of *Hibiscus,* botanically known as *Hibiscus rosa-sinensis,* and hereinafter referred to by the name 'YOHIB 2362'.

The new *Hibiscus* is a product of a planned breeding program conducted by the Inventor in Alva, Fla. The objective of the breeding program is to create new freely-branching *Hibiscus* cultivars with a dense, uniform and compact plant habit appropriate for container production, early and uniform flowering, numerous flowers per lateral branch, desirable flower color and good postproduction longevity.

The new *Hibiscus* originated from a cross-pollination made by the Inventor in Alva, Fla. in late 1998, of a proprietary *Hibiscus rosa-sinensis* selection, designated as code number YB-1460, not patented, as the female, or seed, parent with a proprietary *Hibiscus rosa-sinensis* selection, designated as code number YB-1593, not patented, as the male, or pollen, parent. The cultivar YOHIB 2362 was discovered and selected by the Inventor as a flowering plant within the progeny of the stated cross-pollination in a controlled environment in Alva, Fla., on Oct. 11, 2000.

Asexual reproduction of the new *Hibiscus* by vegetative terminal cuttings in a controlled environment in Alva, Fla.

since February, 2001, has shown that the unique features of this new *Hibiscus* are stable and reproduced true to type in successive generations.

SUMMARY OF THE INVENTION

The cultivar YOHIB 2362 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'YOHIB 2362'. These characteristics in combination distinguish 'YOHIB 2362' as a new and distinct cultivar:

1. Upright, outwardly spreading, uniform, dense and symmetrical plant habit that is appropriate for container production.
2. Glossy dark green-colored leaves.
3. Uniform and freely flowering habit.
4. Large bright yellow-colored flowers with dark red-colored centers.
5. Good resistance to flower bud abscission during shipping.
6. Tolerant to pathogens common to *Hibiscus* grown under Florida production conditions.

Plants of the new *Hibiscus* can be compared to plants of the female parent, the proprietary *Hibiscus* selection code number YB-1460. Plants of the new *Hibiscus* differ from plants of the female parent selection in the following characteristics:

1. Plants of the new *Hibiscus* are more upright than plants of the female parent selection.

2. Plants of the new *Hibiscus* have darker green-colored foliage than plants of the female parent selection.
3. Plants of the new *Hibiscus* and the female parent selection differ in flower coloration as flowers of plants of the female parent selection have white-colored bands around red-colored centers.

Plants of the new *Hibiscus* can be compared to plants of the male parent, the proprietary *Hibiscus* selection code number YB-1593. Plants of the new *Hibiscus* differ from plants of the male parent selection in the following characteristics:

1. Plants of the new *Hibiscus* are not as vigorous as plants of the male parent selection.
2. Plants of the new *Hibiscus* have a more uniform plant habit than plants of the male parent selection.
3. Plants of the new *Hibiscus* and the male parent selection differ in flower coloration as plants of the male parent selection have darker yellow-colored flowers with orange-colored bands around red-colored centers.

Plants differ from plants of the *Hibiscus* cultivar 'Montego Wind', disclosed in a U.S. Plant patent application filed concurrently, primarily in flower color.

Plants of the new *Hibiscus* can be compared to plants of the *Hibiscus* cultivar Sundance, not patented. In side-by-side comparisons conducted in Alva, Fla., plants of the new *Hibiscus* differed from plants of the cultivar Sundance in the following characteristics:

1. Plants of the new *Hibiscus* were more freely branching than plants of the cultivar Sundance.
2. Plants of the new *Hibiscus* were more freely flowering than plants of the cultivar Sundance.
3. Plants of the new *Hibiscus* had darker yellow-colored flower than plants of the cultivar Sundance.

BRIEF DESCRIPTION OF THE PHOTOGRAPH

The accompanying colored photograph illustrates the overall appearance of the new *Hibiscus,* showing the colors as true as it is reasonably possible to obtain in colored reproductions of this type. Colors in the photograph may differ slightly from the color values cited in the detailed botanical description which accurately describe the colors of the new *Hibiscus*. The photograph is a close-up view of a typical flower of 'YOHIB 2362'.

DETAILED BOTANICAL DESCRIPTION

The photographs and following observations, measurements and values describe plants grown in Alva, Fla., with five plants per 16.5-cm container in polyethylene-covered greenhouses during the late summer under conditions which closely approximate commercial production. During the production of the plants, day temperatures ranged from 16 to 37° C. and night temperatures ranged from 13 to 26° C. Plants were about four months old when the photographs and the description were taken. In the description, color references are made to The Royal Horticultural Society Colour Chart, 1995 Edition, except where general terms of ordinary dictionary significance are used.

Botanical classification: *Hibiscus rosa-sinensis* cultivar YOHIB 2362.

Parentage:

*Female or seed parent.*—Proprietary selection of *Hibiscus rosa-sinensis* designated as code number YB-1460, not patented.

*Male or pollen parent.*—Proprietary selection of *Hibiscus rosa-sinensis* designated as code number YB-1593, not patented.

Propagation:

*Type.*—By vegetative terminal cuttings.

*Time to initiate roots.*—About 10 days at temperatures of 24° C.

*Time to develop roots.*—About four weeks at temperatures of 24° C.

*Root description.*—Thick, fibrous; white in color.

*Rooting habit.*—Somewhat freely branching; moderately dense.

Plant description:

*Plant form and growth habit.*—Perennial, evergreen, upright, outwardly spreading, uniform, dense and symmetrical plant habit; inverted triangle. Vigorous growth habit.

*Branching habit.*—Freely branching, usually about three or four lateral branches develop after removal of terminal apex.

*Plant height.*—About 29 cm.

*Plant diameter* (*area of spread*).—About 45 cm.

*Lateral branch description.*—Length: About 27 cm. Diameter: About 7 mm. Internode length: About 4.2 cm. Strength: Strong, but flexible. Texture: Immature, pubescent; mature, woody and rough. Color: Immature: Close to 146A. Mature: Close to 197A.

*Foliage description.*—Arrangement: Alternate, single; numerous; symmetrical. Length: About 7.7 cm. Width: About 6.9 cm. Shape: Ovate to cordate. Apex: Acute; typically reflexed. Base: Cordate. Margin: Crenate. Texture, upper and lower surfaces: Smooth to sparsely pubescent; rough; leathery. Luster, upper and lower surfaces: Glossy. Venation pattern: Palmate. Color: Developing and fully expanded foliage, upper surface: Darker green than 147A. Developing and fully expanded foliage, lower surface: Close to 147A. Venation, upper surface: 147A to darker green than 147A. Venation, lower surface: Close to 147A. Petiole: Length: About 3.7 cm. Diameter: About 3.25 mm. Texture, upper and lower surfaces: Pubescent. Color, upper and lower surfaces: 147A slightly overlain with close to 187A.

Flower description:

*Flower arrangement.*—Flowers arranged singly at terminal leaf axils. Freely flowering with usually about two or three flower buds and/or open flowers per terminal apex. Flowers face upright to outwardly.

*Flower appearance.*—Rounded, bright yellow-colored flowers with dark red-colored centers. Flowers are open for about two days. Flowers persistent.

*Fragrance.*—None detected.

*Natural flowering season.*—Usually spring and summer or during periods of warm weather.

*Flower bud* (*before stage of showing color*).—Resistance to abscission during shipping: Plants of the new *Hibiscus* have been observed to resist flower bud drop when stored in a closed box for 5 days at 13° C. Length: About 2.2 cm. Diameter: About 1.25 cm. Shape: Ovoid. Color: More green than 147A.

*Flower diameter.*—Large, about 14 cm.

*Flower length* (*height*).—About 9 cm.

*Petals.*—Arrangement: Corolla consists of five petals that are fused at base; petals imbricate. Length: About 9.5 cm. Width: About 7.2 cm. Shape: Roughly obovate to spatulate. Apex: Rounded. Base: Attenuate. Margin: Entire; somewhat ruffled. Texture, upper and lower surfaces: Smooth, glabrous, satiny; center, waxy. Color: When opening and fully opened, upper surface: Close to 9A; center, 45A to 46A. When opening and fully opened, lower surface: Close to 9C.

*Sepals.*—Appearance: Five sepals fused into a tubular star-shaped calyx. Length: About 2.75 cm. Width: About 1.3 cm. Shape: Oblong. Apex: Cuspidate. Margin: Entire. Texture, upper surface: Smooth; waxy. Texture, lower surface: Sparsely pubescent. Color, upper surface: Close to 146B. Color, lower surface: Close to 146A.

*Flower bracts.*—Appearance: About eight fused at base. Length: About 1.4 cm. Width: About 6.5 mm. Shape: Lanceolate. Apex: Sharply acute. Margin: Entire. Texture, upper surface: Smooth, glabrous. Texture, lower surface: Sparsely pubescent. Color, upper surface: Close to 146A. Color, lower surface: Close to 147A.

*Peduncles.*—Length: About 1.25 cm. Diameter: About 3 mm. Angle: Straight to slightly bent. Strength: Strong, flexible. Texture: Sparsely pubescent. Color: Close to 146A.

*Reproductive organs.*—Androecium: Stamen number: Numerous, about 50. Filament length: About 5 mm. Filament color: Close to 17A. Anther shape: Reniform. Anther size: About 2 mm by 1.5 mm. Anther color: Close to 17A. Amount of pollen: Abundant. Pollen color: Close to 17A. Gynoecium: Pistil length: About 9.1 cm. Style length: About 7.4 cm. Style texture: Smooth, waxy. Style color: 17A; towards the base, 17A overlain with 45A to 46A. Stigma appearance: Five, rounded. Stigma color: Close to 45A. Ovary color: Close to 154C.

*Seed/fruit.*—Seed and fruit production has not been observed.

Temperature tolerance: Plants of the new *Hibiscus* have been observed to tolerate temperatures from 0 to 38° C.

Disease/pest tolerance: Plants of the new *Hibiscus* grown under Florida production conditions have shown to be relatively tolerant to pathogens common to *Hibiscus* such as Pseudomonas, Pythium and Phytophthora. Plants of the new *Hibiscus* have not been observed to be tolerant to pests and other pathogens.

It is claimed:

1. A new and distinct *Hibiscus* plant named 'YOHIB 2362', as illustrated and described.

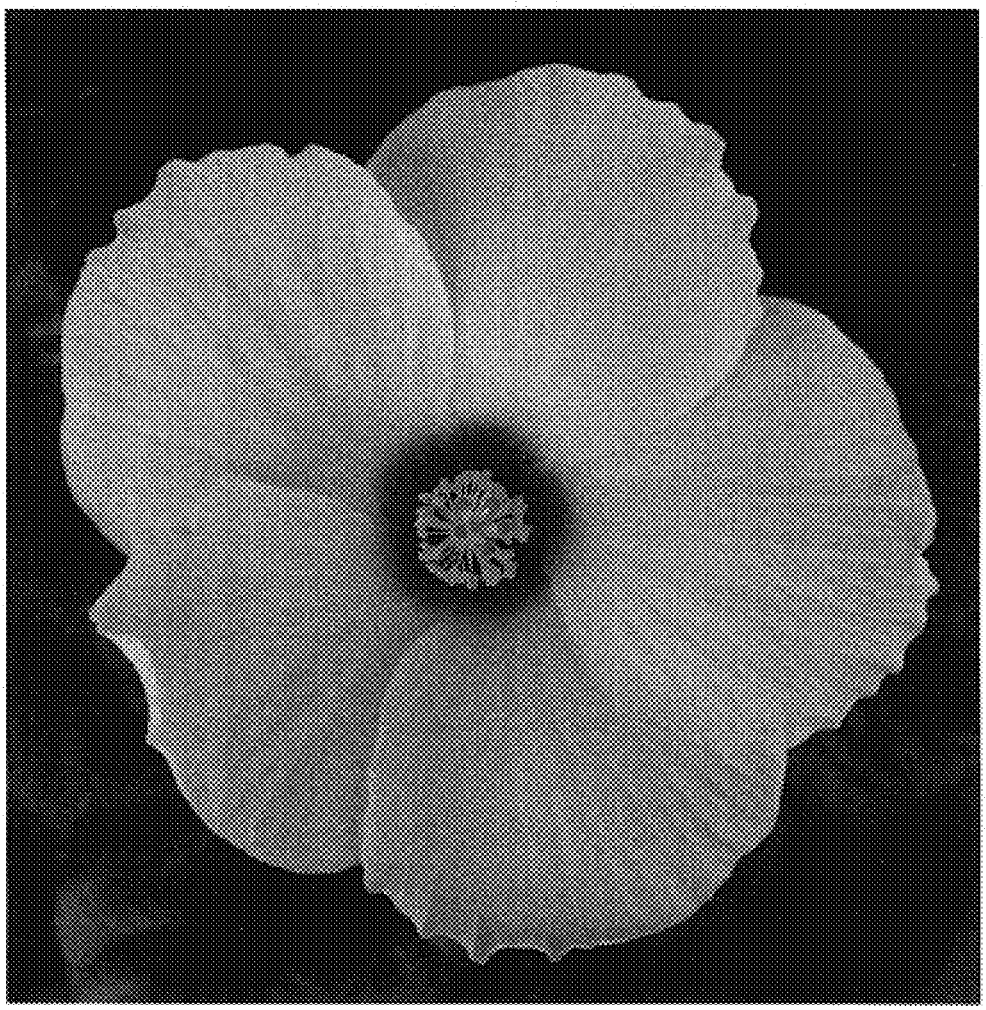

* * * * *